United States Patent [19]

Tronich et al.

[11] 4,410,707
[45] Oct. 18, 1983

[54] PROCESS FOR THE MANUFACTURE OF 3-AMINO-1-PHENYLPYRAZOL-5-ONE

[75] Inventors: Wolfgang Tronich, Eppstein; Wolfgang Rieper, Frankfurt am Main; Peter Böhme, Kelkheim, all of Fed. Rep. of Germany

[73] Assignee: Hoechst Aktiengesellschaft, Frankfurt am Main, Fed. Rep. of Germany

[21] Appl. No.: 285,469

[22] Filed: Jul. 21, 1981

[30] Foreign Application Priority Data

Jul. 23, 1980 [DE] Fed. Rep. of Germany ....... 3027845

[51] Int. Cl.$^3$ ............................................ C07D 231/52
[52] U.S. Cl. .................................................... 548/360
[58] Field of Search ......................................... 548/360

[56] References Cited

PUBLICATIONS

Porter et al., Organic Syntheses 1948, vol. 28, pp. 87–89.

Primary Examiner—Henry R. Jiles
Assistant Examiner—Natalia Harkaway
Attorney, Agent, or Firm—Curtis, Morris & Safford

[57] ABSTRACT

The preparation of 3-amino-1-phenylpyrazol-5-one by heating phenylhydrazine and a lower cyanoacetic acid alkyl ester in a polar solvent, using a lower alcoholate of an alkali metal as the condensation agent, leads to particularly high yields and quality, if the phenylhydrazine and 1 to 1.2 moles of the alcoholate are initially taken, the cyanoacetic ester is metered in and the reaction is carried out at 105° to 140° C., volatile alcohols which have been liberated from the ester and, if appropriate, from the alcoholate being distilled off at the reaction temperature. It is advantageous to employ the phenylhydrazine in an excess of up to about 200 mole % and to select, as the polar solvent, an alcohol or ether having a boiling point above 105° C.

11 Claims, No Drawings

PROCESS FOR THE MANUFACTURE OF 3-AMINO-1-PHENYLPYRAZOL-5-ONE

The preparation of 3-amino-1-phenylpyrazol-5-one from one mole of cyanoacetic acid ethyl ester, one mole of phenylhydrazine and two moles of sodium ethylate is described in Org. Synth., Coll. Vol. 3, 708–709. In this process, the cyanoacetic ester is first added to a hot solution of sodium ethylate in ethanol and the phenylhydrazine is then added, the mixture is heated at 120° C. for 16 hours under pressure and while stirring, the ethanol is largely removed by distillation in vacuo, water is added to the residue, the mixture is extracted several times with ether, the aqueous phase is acidified with glacial acetic acid and the precipitated product is first washed with ethanol and then extracted by boiling with ethanol, cooled and washed again with ethanol and dried. This gives a brown product having a melting point of 216° to 218° C. (with decomposition) in a yield of 43 to 47%. The comment is made that a very strongly colored product is obtained in most cases if, instead of the working-up procedure described, water is added to the reaction mixture immediately after the period of heating for 16 hours and the solution is acidified. It is also emphasized that at least two equivalents of sodium ethylate are required for the reaction, but that larger quantities do not improve the yield.

It has now been found, surprisingly, that the product can be obtained in a better quality and better yield, using only 1 to 1.2 moles of the alcoholate, if the cyanoacetic ester is metered into a previously made up mixture of phenylhydrazine and alcoholate in a polar solvent.

The invention relates, therefore, to a process for the manufacture of 3-amino-1-phenylpyrazol-5-one by heating phenylhydrazine and a lower cyanoacetic acid alkyl ester in a polar solvent, using a lower alcoholate of an alkali metal as the condensation agent, which comprises initially taking the phenylhydrazine and 1 to 1.2 moles of the alcoholate, metering in the cyanoacetic ester and carrying out the reaction at 105° to 140° C., volatile alcohols which have been liberated from the ester and, if appropriate, from the alcoholate being distilled off at the reaction temperature.

In this process the process product is obtained in a good yield and in the form of nearly colorless crystals after a reaction time of only a few hours. The purity of the product is so high that it can be employed without further purification for any requirement.

Preferred embodiments of the invention are described in greater detail below:

It has been found that the yields can be increased considerably if the phenylhydrazine is employed in excess. Thus even an excess of 10 mole % of phenylhydrazine produces a yield of over 50% of theory, while an excess of about 200 mole % produces a yield of the order of magnitude of 70% of theory. On the basis of economic considerations, an excess of about 10 to about 80 mole % is particularly preferred.

Suitable polar solvents are any organic substances which have a suitable solvent power and an adequate stability towards the alkali metal alcoholate at the reaction temperatures. Alcohols or ethers having a boiling point above 105° C. are preferred, for example alkanols having at least 4 carbon atoms, and glycols and also ethers thereof, for example diethylene diglycol, diethylene glycol monoethers and diethylene glycol diethers n-Butanol and, in particular, isobutanol are particularly preferred.

Preferred esters of cyanoacetic acid are the lower alkyl esters, particularly the methyl and ethyl ethers. If esters of alcohols having a boiling point above 105° C. are employed in conjunction with suitable alcoholates, it becomes unnecessary to remove the alcohol liberated in the reaction.

The alkali metal alcoholate used is preferably a lower sodium alkanolate, in particular sodium methylate. The alcoholate can be employed in the solid form, but is advantageously employed as a solution, preferably in the alcohol on which it is based. Sodium methylate in the form of an approximately 30% strength solution in methanol is particularly preferred. It has been found, surprisingly, not only that approximately stoichiometric quantities of alcoholate are sufficient in carrying out the reaction according to the invention, but that the quantity of 2 moles regarded as necessary in accordance with the state of the art actually leads to lower yields.

In carrying out the reaction in accordance with the invention, a high yield is achieved, after a few hours, even at temperatures which are markedly below the 120° C. of the known process. Temperatures higher than 140° C. are not advantageous. Pressure is not required.

In a particularly preferred embodiment, isobutanol is initially taken, about 1.1 moles of sodium methylate are added, in the form of an approximately 30% strength solution in methanol, and the methanol is largely removed by distillation at temperatures up to about 115° C. Excess phenylhydrazine is added and cyanoacetic acid methyl ester is added dropwise at a temperature of about 105° to about 115° C. The methanol liberated is distilled off continuously; the reaction is complete when methanol no longer passes over. This is the case after about 2 to 3 hours.

The reaction mixture is appropriately worked up by mixing it with water, advantageously by pouring it into water, and the product is precipitated with acid. In so doing, it is preferable not to let the pH fall below a value of 6. It is advantageous if a reducing agent is added to the water before or during the precipitation, for example an alkali metal sulfite, disulfite or dithionite, particularly sodium dithionite.

Any sufficiently strong organic or inorganic acid can be used for the precipitation; mineral acids, such as hydrochloric acid, are preferred. It is preferable to discontinue the precipitation when a pH value of 6.5 has been reached and to isolate the product by filtration.

If a solvent which is slightly miscible with water is used, for example isobutanol, it has proved appropriate to add a water-soluble alcohol, preferably alcohol which has been liberated in the reaction and distilled off, and only then to mix the reaction mixture with water. A particularly pure product is obtained in this way.

In the examples which follow, unless otherwise specified, parts and percentages relate to weight. All the reactions were carried out under nitrogen.

EXAMPLES 300 parts of isobutanol and 250 parts of an approximately 30% strenght solution of sodium methylate in methanol (1.1 moles) are initially placed in a stirred flask. The methanol is largely distilled off via a packed column at a sump product temperature of 115° C. and the quantity of phenylhydrazine indicated below is then run in. 125 parts (1 mole) of cyanoacetic acid methyl ester are then added dropwise in the course of about 2 hours, and isobutanol containing methanol is distilled off continuously. When no further distillate passes over at a maximum sump product temperature of 115° C., the reaction is complete.

The distillate is now run back into the mixture, which is stirred into about 380 parts of water, and the pH is adjusted to a value of 6.5 with hydrochloric acid. The precipitated product is filtered off, washed with water and dried in vacuo. 3-Amino-1-phenylpyrazol-5-one is obtained in the form of slightly cream-colored crystals in a form which is pure according to thin layer chromatography. Its melting point is 218°–219° C.

| Example | Moles of phenylhydrazine | Yield (% of theory) |
| --- | --- | --- |
| 1 | 1.0 | 47.0 |
| 2 | 1.1 | 52.0 |
| 3 | 1.2 | 54.0 |
| 4 | 1.8 | 62.4 |
| 5 | 3 | 68.1 |

COMPARISON EXAMPLES

EXAMPLE 6

If the reaction is carried out in accordance with Example 2, but using 2 moles of sodium methylate, the yield is only 44% of theory.

EXAMPLE 7

If the reaction is carried out in accordance with Example 2, but in a closed vessel, that is to say without distilling off the methanol, a yield of 41% of theory is obtained after heating at 125° C. for 3 hours. The product has a brown color.

EXAMPLE 8

If Example 2 is repeated, but using 300 parts of methanol instead of the isobutanol employed, and if the reaction is carried out at 125° C. for 3 hours in an autoclave, a yield of only 30% of theory is obtained.

EXAMPLE 9

If the reaction is carried out in accordance with Example 2, but all the components are added together at the start of the reaction and all the methanol is distilled off in the course of 6 hours, a yield of only 34% of theory is obtained.

We claim:

1. In a process for the manufacture of 3-amino-1-phenyl-pyrazol-5-one by heating phenylhydrazine and a lower cyanoacetic acid alkyl ester in a polar solvent with a lower alcoholate of an alkali metal as the condensation agent, the improvement comprising initially taking the phenylhydrazine in an excess of 10 to 200 mole % and 1 to 1.2 moles of the alcoholate, each per mole of lower cyanoacetic acid alkyl ester, metering in the cyanoacetic ester and carrying out the reaction at 105° to 140° C., volatile alcohols which have been liberated being distilled off at the reaction temperature, and subsequently mixing the reaction mixture with water and precipitating the 3-amino-1-phenyl-pyrazol-5-one with an inorganic or organic acid at a pH value not less than 6.

2. A process as claimed in claim 1, wherein an excess of 10 to 80 mole % of phenylhydrazine is employed.

3. A process as claimed in claim 1, wherein the polar solvent is an alcohol or ether having a boiling point above 105° C.

4. A process as claimed in claim 1, wherein the solvent is isobutanol.

5. A process as claimed in claim 1, wherein cyanoacetic acid methyl ester is reacted in the presence of sodium methylate.

6. A process as claimed in claim 1, wherein methanolic sodium methylate solution is isobutanol is initially taken and is distilled so that it is largely free from methanol, the phenylhydrazine is added, cyanoacetic acid methyl ester is metered in and the ethanol liberated is distilled off.

7. A process as claimed in claim 1, wherein a reducing agent is added before or during the precipitation.

8. A process as claimed in claim 1, wherein, the solvent which is slightly miscible with water and, the volatile alcohol which has been removed by distillation is added to the reaction mixture before the latter is mixed with water.

9. A process for the manufacture of 3-amino-1-phenylpyrazol-5-one comprising
   metering a lower cyanoacetic acid alkyl ester into a mixture, in a polar solvent, of phenylhydrazine in an excess of 10 up to about 200 mole % and 1 to 1.2 moles of a lower alcoholate of an alkali metal per mole of lower cyanoacetic acid alkyl ester; and
   reacting the resulting mixture at a temperature of 105° to 140° C., while the volatile alcohols are distilled off at the reaction temperature, to form 3-amino-1-phenylpyrazol-5-one.

10. The process according to claim 9, wherein the phenylhydrazine is employed in an excess of 10 to about 80 mole percent.

11. The process according to claim 10, wherein the reaction is carried out at atmospheric pressure for a period of about 2 to 3 hours.

* * * * *